(12) United States Patent
Toyama et al.

(10) Patent No.: US 11,117,089 B2
(45) Date of Patent: Sep. 14, 2021

(54) APPARATUS AND CALCULATING METHOD OF PH

(71) Applicant: FUJI ELECTRIC CO., LTD., Kanagawa (JP)

(72) Inventors: Hiroyuki Toyama, Suginami-ku (JP); Kuniyuki Takahashi, Hino (JP)

(73) Assignee: FUJI ELECTRIC CO., LTD., Kanagawa (JP)

( * ) Notice: Subject to any disclaimer, the term of this patent is extended or adjusted under 35 U.S.C. 154(b) by 153 days.

(21) Appl. No.: 16/663,311

(22) Filed: Oct. 24, 2019

(65) Prior Publication Data
US 2020/0054990 A1 Feb. 20, 2020

Related U.S. Application Data

(63) Continuation of application No. 15/609,046, filed on May 31, 2017, now Pat. No. 10,456,733, and a (Continued)

(30) Foreign Application Priority Data

Mar. 16, 2015 (JP) ................. 2015-052204

(51) Int. Cl.
*B01D 53/14* (2006.01)
*B01D 53/34* (2006.01)
(Continued)

(52) U.S. Cl.
CPC ......... *B01D 53/1412* (2013.01); *B01D 53/14* (2013.01); *B01D 53/1456* (2013.01);
(Continued)

(58) Field of Classification Search
CPC .... B01D 2252/1035; B01D 2258/0283; B01D 2259/4566; B01D 53/14; B01D 53/1412;
(Continued)

(56) References Cited

U.S. PATENT DOCUMENTS

| 2010/0206171 | A1 | 8/2010 | Peng |
| 2015/0007719 | A1* | 1/2015 | Langh ............... B01D 53/1425 95/9 |
| 2015/0209720 | A1 | 7/2015 | Komatsu |

FOREIGN PATENT DOCUMENTS

| CN | 102112210 A | 6/2011 |
| CN | 102337948 A | 2/2012 |

(Continued)

OTHER PUBLICATIONS

Google search—ship scrubber ph meter controller Year: 2021.*
(Continued)

*Primary Examiner* — Cabrena Holecek (57) ABSTRACT

A human load of regularly measuring a pH of a position 4 meters from a discharge point during a term of a commissioning of a ship with a scrubber apparatus is reduced. Provided is an apparatus provided inside a ship having a scrubber, including a first pH measuring instrument which measures a pH value of washing water discharged from the scrubber to outboard, a second pH measuring instrument which measures a pH value of washing water supplied from outboard to the scrubber, and a calculating unit which calculates a pH value of water at a predetermined position outboard, based on a dilution ratio which shows a ratio by which the washing water discharged to outboard is diluted at the predetermined position outboard, the pH value measured by the first pH measuring instrument, and the pH value measured by the second pH measuring instrument.

8 Claims, 4 Drawing Sheets

Related U.S. Application Data continuation of application No. PCT/JP2016/053582, filed on Feb. 5, 2016.

(51) Int. Cl.

| | | |
|---|---|---|
| *B01D 53/50* | (2006.01) | |
| *B01D 53/92* | (2006.01) | |
| *B63H 21/32* | (2006.01) | |
| *B63H 21/38* | (2006.01) | |
| *B63J 3/04* | (2006.01) | |
| *F01N 3/04* | (2006.01) | |
| *G01N 1/28* | (2006.01) | |
| *G01N 27/416* | (2006.01) | |
| *G01N 33/18* | (2006.01) | |

(52) U.S. Cl.
CPC ....... *B01D 53/1493* (2013.01); *B01D 53/346* (2013.01); *B01D 53/50* (2013.01); *B01D 53/504* (2013.01); *B01D 53/92* (2013.01); *B63H 21/32* (2013.01); *B63H 21/38* (2013.01); *B63J 3/04* (2013.01); *F01N 3/04* (2013.01); *G01N 1/28* (2013.01); *G01N 27/4167* (2013.01); *G01N 33/18* (2013.01); *B01D 2252/1035* (2013.01); *B01D 2258/0283* (2013.01); *B01D 2259/4566* (2013.01)

(58) Field of Classification Search
CPC ............ B01D 53/1456; B01D 53/1493; B01D 53/346; B01D 53/50; B01D 53/504; B01D 53/92; B63H 21/32; B63H 21/38; B63J 3/04; F01N 3/04; G01N 1/28; G01N 27/4167; G01N 33/18
See application file for complete search history.

(56) References Cited

FOREIGN PATENT DOCUMENTS

| | | |
|---|---|---|
| CN | 104168976 A | 11/2014 |
| CN | 204107298 U | 1/2015 |
| CN | 104919151 A | 9/2015 |
| EP | 2955345 A1 | 12/2015 |
| JP | S61181593 A | 8/1986 |
| JP | 2008029975 A | 2/2008 |
| JP | 2011524800 A | 9/2011 |
| JP | 2013154330 A | 8/2013 |
| WO | 2006018911 A1 | 2/2006 |
| WO | 2014118819 A1 | 8/2014 |
| WO | 2014119513 A1 | 8/2014 |

OTHER PUBLICATIONS

International Search Report for International Patent Application No. PCT/JP2016/053582, issued by the Japan Patent Office dated Mar. 29, 2016.
The Marine Environment Protection Committee(MEPC), "MEPC 59/24/Add.1",p. 1-p. 24, Adopted on Jul. 17, 2009.
Anders Andreasen et al. "Use of Seawater Scrubbing for SO2 Removal from Marine Engine Exhaust Gas". pp. 3274?3279, published on Oct. 19, 2007.
International Maritime Organization,"IMO PPR2 Results of deliberation", p. 2 (2), Jan. 26, 2015.
Extended European Search Report for European Patent Application No. 16 764 572.0, issued by the European Patent Office dated Sep. 6, 2017.
Office Action issued for counterpart Chinese Application No. 201680003881.X, issued by the State Intellectual Property Office dated Nov. 19, 2018.
U.S. Appl. No. 15/609,046, filed May 31, 2017, to Hiroyuki Toyama et al.

\* cited by examiner

APPARATUS AND CALCULATING METHOD OF PH

CROSS-REFERENCE TO RELATED APPLICATIONS

This application is a continuation of U.S. patent application Ser. No. 15/609,046, filed on May 31, 2017, which is a continuation of International Patent Application No. PCT/JP2016/053582, filed on Feb. 5, 2016, which claims priority to Japanese Patent Application No. 2015-052204, filed on Mar. 16, 2015, the contents of each of which are incorporated herein by reference in their entirety.

BACKGROUND

1. Technical Field

The present invention relates to an apparatus and a calculating method of pH.

A pH of a sulfur absorbing liquid which is sea water having absorbed sulfur is around 3. In order to discharge the sulfur absorbing liquid to the sea, the pH must be raised. Conventionally, the pH value has been raised by exposing the sulfur absorbing liquid in the air in an aeration apparatus (for instance, refer to WO No. 2006/018911).

2. Related Art

A guideline related to environmental regulations when discharging the sea water having absorbed sulfur oxides to the sea is established. According to the guideline MEPC 59/24/Add.1, "During commissioning of the exhaust gas cleaning unit(s) after installation, the discharged washwater plume should be measured externally from the ship (while being at anchor) and the discharge pH at the ship's overboard pH monitoring point will be recorded when the plume at 4 metres from the discharge point equals or is above pH 6.5." The commissioning at the time of installing the exhaust gas cleaning apparatus extends over several days. During the term of the commissioning, various tests such as changing the engine load and operating the exhaust gas cleaning apparatus are performed. During the term of the commissioning, it is thought that a person regularly measures a pH of the position 4 meters from the discharge point, but a human load of this measuring method is large.

SUMMARY

An apparatus provided inside a ship having a scrubber in a first aspect of the present invention includes a first pH measuring instrument, a second pH measuring instrument, and a calculating unit. The first pH measuring instrument may measure a pH value of washing water discharged from the scrubber to outboard. The second pH measuring instrument may measure a pH value of washing water supplied from outboard to the scrubber. The calculating unit may calculate a pH value of water at a predetermined position outboard, based on a dilution ratio which shows a ratio by which the washing water discharged to outboard is diluted at the predetermined position outboard, the pH value measured by the first pH measuring instrument, and the pH value measured by the second pH measuring instrument.

The calculating unit may calculate a value of the dilution ratio in advance, based on a first pH value measured by the first pH measuring instrument, a second pH value measured by the second pH measuring instrument, and a third pH value of the water at the predetermined position outboard. The apparatus may further include a recording unit. The recording unit may be connected to the calculating unit. The recording unit may record the value of the dilution ratio. The calculating unit may calculate the pH value of the water at the predetermined position, based on a pH value measured by the first pH measuring instrument after measuring the first pH value, a pH value measured by the second pH measuring instrument after measuring the second pH value, and the value of the dilution ratio recorded in the recording unit.

The calculating unit may calculate the dilution ratio, using pH1 which is the first pH value, pH2 which is the second pH value, and pH3 which is the third pH value, by $\alpha = (10^{-pH1} - 10^{-pH2})/(10^{-pH3} - 10^{-pH2})$.

The calculating unit may calculate in advance a value of a first dilution ratio calculated based on the pH1, the pH2, and the pH3 when a flow rate of washing water discharged from the scrubber to outboard is a first flow rate, and a value of a second dilution ratio calculated based on the pH1, the pH2, and the pH3 when the flow rate of the washing water discharged from the scrubber to outboard is a second flow rate. The recording unit may record the value of the first dilution ratio and the value of the second dilution ratio. The calculating unit may calculate the pH value of the water at the predetermined position, using the value of the dilution ratio corresponding to the flow rate of the washing water discharged from the scrubber to outboard. The recording unit may record and associate the flow rate of the washing water and the value of the dilution ratio.

The apparatus may further include a controlling unit. The controlling unit may control a flow rate of washing water supplied to the scrubber, depending on the pH value of the water at the predetermined position calculated by the calculating unit. If the flow rate of the washing water supplied to the scrubber is larger than or equal to a predetermined allowable amount, the controlling unit may control the flow rate of the washing water supplied to the scrubber to be smaller than or equal to the allowable amount, by decreasing an output of a motor which discharges exhaust gas to the scrubber. Provided that the ship is determined to be at anchor, the controlling unit may decrease the output of the motor which discharges the exhaust gas to the scrubber.

A calculating method of pH of water at a predetermined position outside a ship having a scrubber in a second aspect of the present invention includes measuring a pH value of washing water discharged from the scrubber to outboard, measuring a pH value of washing water supplied from outboard to the scrubber, and calculating the pH value of the water at the predetermined position outboard, based on a dilution ratio which shows a ratio by which the washing water discharged to outboard is diluted at the predetermined position outboard, the pH value measured in the measuring of the pH value of the washing water discharged from the scrubber to outboard, and the pH value measured in the measuring of the pH value of the washing water supplied from outboard to the scrubber.

The calculating method of pH may be performed at a time of commissioning of the ship having the scrubber. The calculating method of pH may further include, before the calculating of the pH value of the water at the predetermined position outboard, calculating a value of the dilution ratio in advance, based on a first pH value, a second pH value, and a third pH value, and recording the value of the dilution ratio. The first pH value may be measured in the measuring of the pH value of the washing water discharged from the scrubber to outboard. The second pH value may be measured in the measuring of the pH value of the washing water discharged from the scrubber to outboard. The third pH value may be the pH value of the water at the predetermined position outboard. The calculating of the pH value of the water at the predetermined position outboard may be calculating the pH value of the water at the predetermined position outboard, based on the pH value of the washing water discharged from the scrubber to outboard which is measured after measuring the first pH value, the pH value of the washing water supplied from outboard to the scrubber which is measured after measuring the second pH value, and the value of the dilution ratio recorded.

The calculating of the value of the dilution ratio in advance may have calculating a value of a first dilution ratio, and a value of a second dilution ratio. The value of the first dilution ratio may be calculated based on the first pH value, the second pH value, and the third pH value when a flow rate of the washing water discharged from the scrubber to outboard is a first flow rate. The value of the second dilution ratio may be calculated based on the first pH value, the second pH value, and the third pH value when the flow rate of the washing water discharged from the scrubber to outboard is a second flow rate. The recording of the value of the dilution ratio may have recording the value of the first dilution ratio and the value of the second dilution ratio. The calculating method of pH may further include calculating the pH value of the water at the predetermined position outboard, using the value of the dilution ratio corresponding to the flow rate of the washing water discharged from the scrubber to outboard.

The calculating method of pH may further include controlling a flow rate of the washing water supplied to the scrubber, depending on the pH value calculated in the calculating of the pH value of the water at the predetermined position outboard. The calculating method of pH may further include, if the flow rate of the washing water supplied to the scrubber is larger than or equal to a predetermined allowable amount, decreasing an output of a motor which discharges exhaust gas to the scrubber to control the flow rate of the washing water supplied to the scrubber to be smaller than or equal to the allowable amount. The calculating method of pH may further include, provided that the ship is determined to be at anchor, decreasing an output of a motor which discharges exhaust gas to the scrubber.

The summary clause does not necessarily describe all necessary features of the embodiments of the present invention. The present invention may also be a sub-combination of the features described above.

DESCRIPTION OF EXEMPLARY EMBODIMENTS

Hereinafter, the present invention is described through the embodiments of the invention. However, the following embodiments do not limit the invention according to the claims. Also, all the combinations of the features described in the embodiments are not necessarily essential for means provided by aspects of the invention.

Figure 1:
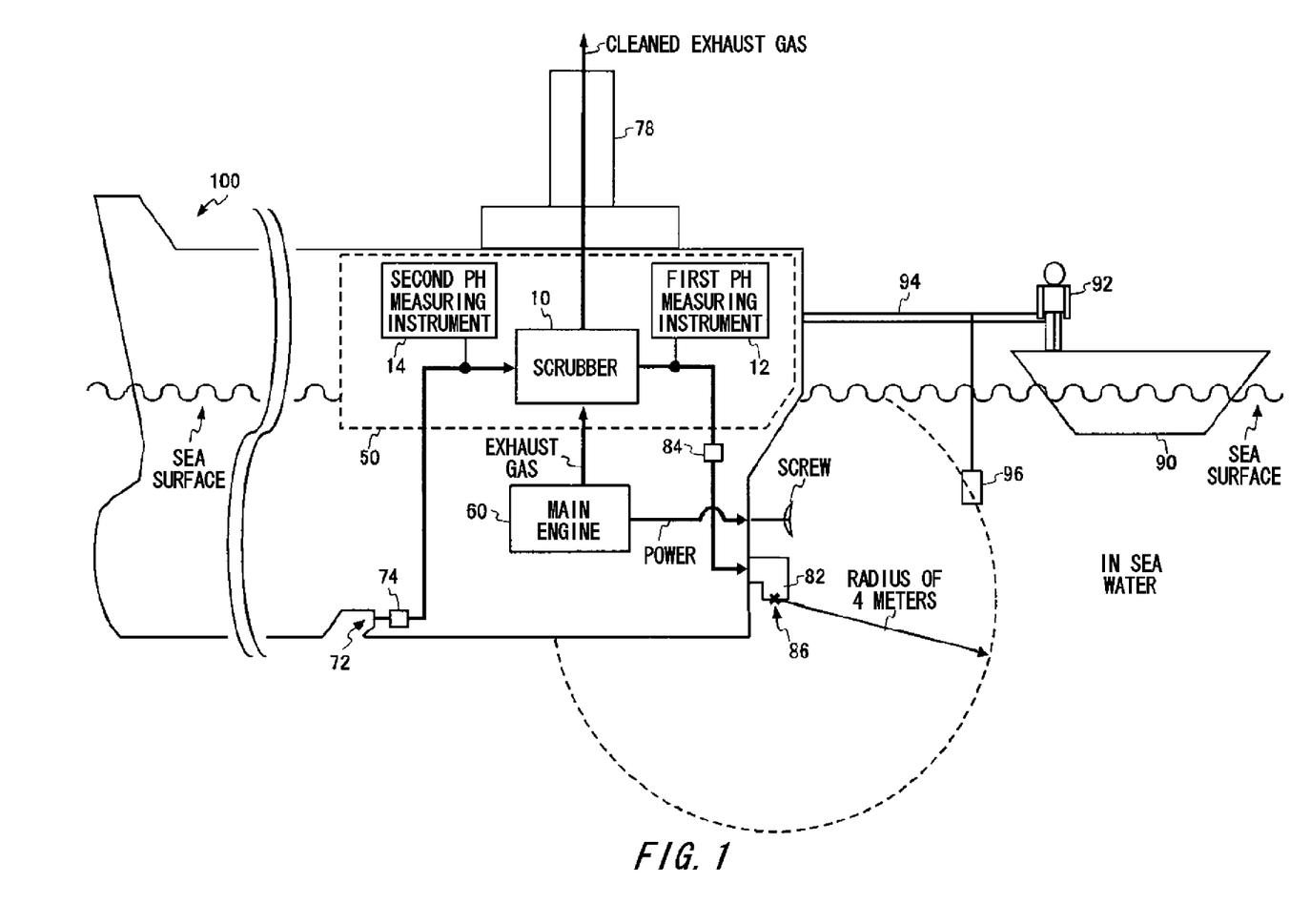
FIG. 1 is a diagram showing a state of sampling sea water of a position 4 meters from a discharge point 86.

FIG. 1 is a diagram showing a state of sampling sea water of a position 4 meters from a discharge point 86. A ship 100 of the present example has, at least, exhaust gas cleaning apparatus 50, a main engine 60, a chimney 78, an inlet opening 72, an intake pump 74, an outlet opening 82, and a discharge pump 84. Note that, the above-described members and portions are merely minimum members and portions necessary for describing the characteristics of the ship 100 of the present example. The ship 100 may have an element other than the above-described members and portions. Also, in FIG. 1, an illustration of the part of the ship 100 between the bow and the stern is omitted due to limitations of space on the sheet of paper.

The main engine 60 as a motor gives a power to a screw of the ship 100. Thereby, the ship 100 obtains a propulsive force. Because heavy oil is combusted in the main engine 60, exhaust gas is generated. The exhaust gas discharged from the main engine 60 enters a scrubber 10 of the exhaust gas cleaning apparatus 50. Note that, the motor may also have another engine other than the main engine 60. In this case, exhaust gas of another engine other than the main engine 60 may also be entered into the scrubber 10.

The exhaust gas cleaning apparatus 50 of the present example is provided inside the ship 100. The exhaust gas cleaning apparatus 50 has, at least, a scrubber 10, a first pH measuring instrument 12, and a second pH measuring instrument 14. The scrubber 10 cleans the exhaust gas discharged from the main engine 60.

The exhaust gas includes sulfur oxides ($SO_x$) and the like. The scrubber 10 decreases the concentration of the sulfur oxides in the exhaust gas, by gas-liquid reacting the exhaust gas including the sulfur oxides and the like and the sea water. Thereby, the scrubber 10 cleans the exhaust gas. The exhaust gas cleaned by the scrubber 10 is discharged outside the ship 100 through the chimney 78.

The intake pump 74 supplies sea water as washing water to the scrubber 10 through the inlet opening 72 from outside the ship 100. The second pH measuring instrument 14 measures a pH value of the sea water. Note that, in the present example, the inlet opening 72 is provided at a ship bottom.

The discharge pump 84 discharges sea water as washing water to outside the ship 100 through the outlet opening 82 from the scrubber 10. The first pH measuring instrument 12 measures a pH value of the sea water after cleaning the exhaust gas. Note that, the outlet opening 82 of the present example is provided at a position that the outlet opening 82 is immersed in sea water. A discharge direction of the outlet opening 82 may be a depth direction in sea water.

An operator 92 boards a small ship 90. The operator 92 identifies a predetermined position outside the ship 100 by a surveying instrument 94. In the present example, the operator 92 identifies a position at a radius 4 meters from a discharge point 86, by the surveying instrument 94. The operator 92 gathers around 500 ml of sea water at the identified position by a sampling container 96. The operator 92 measures a pH value of the gathered sea water by means already known such as a pH meter. Thereby, a pH value of the sea water at the position 4 meters from a discharge point 86 is acquired.

Figure 2:
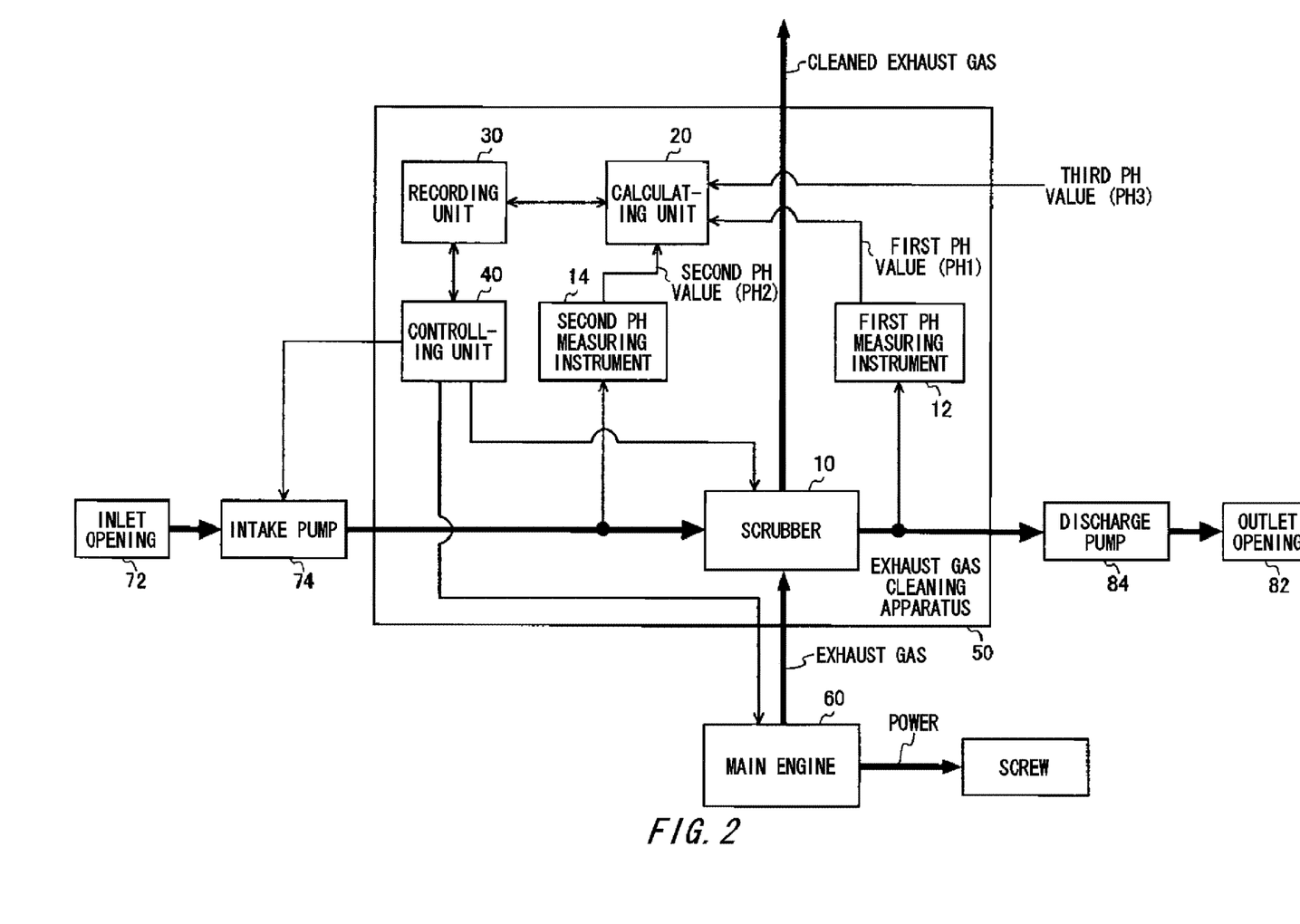
FIG. 2 is a diagram showing details of exhaust gas cleaning apparatus 50.

FIG. 2 is a diagram showing details of exhaust gas cleaning apparatus 50. The exhaust gas cleaning apparatus 50 has a scrubber 10, a first pH measuring instrument 12, a second pH measuring instrument 14, a calculating unit 20, a recording unit 30, and a controlling unit 40. The calculating unit 20, the recording unit 30, and the controlling unit 40 may be configured by a general purpose computer, or may also be configured by connecting a plurality of modules.

The calculating unit 20 calculates a pH value of water at a predetermined position outboard, based on a dilution ratio α which shows a ratio by which washing water discharged to outboard is diluted at the predetermined position outboard, a pH value measured by the first pH measuring instrument 12, and a pH value measured by the second pH measuring instrument 14. Specifically, if the calculating unit 20 already has the information of the dilution ratio α, the calculating unit 20 calculates the pH of the sea water at the position 4 meters from the discharge point 86, which is the predetermined position outboard. Regarding this, the description will be specifically made below.

(Calculation of a Single Dilution Ratio α)

A first pH value measured by the first pH measuring instrument 12 and a second pH value measured by the second pH measuring instrument 14 are inputted to the calculating unit 20. Also, a third pH value of water at the position 4 meters from a discharge point 86, which is measured by the operator 92 by the pH meter and the like, is inputted to the calculating unit 20. The calculating unit 20 calculates in advance a value of a dilution ratio, based on the first pH value, the second pH value, and the third pH value.

Specifically, the calculating unit 20 calculates a dilution ratio α, using a pH1 which is the first pH value, a pH2 which is the second pH value, and a pH3 which is the third pH value, by the following [Expression 1].

$$\alpha = (10^{-pH1} - 10^{-pH2})/(10^{-pH3} - 10^{-pH2})$$ [Expression 1]

If the raw water at the concentration C1 is diluted by the dilution water at the concentration C2, then, as a result, the raw water becomes at the concentration C3, the dilution ratio α becomes the following [Expression 2].

$$\alpha = (C1 - C2)/(C3 - C2)$$ [Expression 2]

In a case of a hydrogen ion concentration Cn, pHn as the pH value becomes the following [Expression 3].

$$pHn = -\log_{10}(Cn)$$ [Expression 3]

If an expression of the [Expression 3] is variated, it becomes the following [Expression 4].

$$Cn = 10^{-pHn}$$ [Expression 4]

Regarding n=1,2,3, the [Expression 4] is respectively substituted into the [Expression 2]. Thereby, it can be understood that the dilution ratio α is expressed like the above [Expression 1].

For instance, if the pH1 measured by the first pH measuring instrument 12 is 6.60, the pH2 measured by the second pH measuring instrument 14 is 9.00, and the pH3 of the sea water of the position 4 meters from the discharge point 86 is 8.35, from the [Expression 1], α=72.2. In the specification, a hydrogen ion concentration of the water which enters the first pH measuring instrument 12 is expressed by C1, a hydrogen ion concentration of the water which enters the second pH measuring instrument 14 is expressed by C2, and a hydrogen ion concentration of the sea water of the position 4 meters from the discharge point 86 is expressed by C3.

(Calculation of pH3)

The recording unit 30 is connected to the calculating unit 20. The recording unit 30 records a value of the dilution ratio α calculated by the calculating unit 20. The calculating unit 20 can exchange data with the recording unit 30. The calculating unit 20 calculates a pH value of water at the predetermined position, based on a pH value measured by the first pH measuring instrument 12 after measuring the first pH value (pH1), a pH value measured by the second pH measuring instrument 14 after measuring the second pH value (pH2), and a value of the dilution ratio α recorded by the recording unit 30.

From the [Expression 2], C3 is expressed by the following [Expression 5].

$$C3 = C2 + (C1 - C2)/\alpha$$ [Expression 5]

For instance, an amount of the exhaust gas which enters the scrubber 10 from the main engine 60 increases, and the pH value measured by the first pH measuring instrument 12 and the pH value measured by the second pH measuring instrument 14 sometimes change. Even in this case, the pH value of the sea water of the position 4 meters from the discharge point 86 can be calculated using the already known dilution ratio α. For instance, because if the pH value measured by the first pH measuring instrument 12 is 5.60, the pH value measured by the second pH measuring instrument 14 is 5.60, α=72.2, so, from [Expression 4] and [Expression 5], the pH value of the sea water of the position 4 meters from the discharge point 86 becomes 7.42.

Therefore, the pH value of the sea water of the predetermined position outboard can be calculated using the pH values newly measured by the first pH measuring instrument 12 and the second pH measuring instrument 14 and the already known dilution ratio α. Thereby, if the dilution ratio α is once measured, by sequentially updating the pH values of the first pH measuring instrument 12 and the second pH measuring instrument 14, pH of the point 4 meters from the discharge point 86 can be known.

(Calculation of a plurality of dilution ratios α1 to αn)

Note that, depending on a load of the main engine 60, the flow rate of washing water discharged from the scrubber 10 to outboard sometimes changes. It is thought that if the washing water flow rate changes, the dilution ratios a also changes. Therefore, the calculating unit 20 may calculate in advance a plurality of dilution ratios α which respectively correspond to different washing water flow rates. That is, the calculating unit 20 may calculate in advance a value of a first dilution ratio α1 calculated based on the pH1, the pH2, and the pH3, if a flow rate of washing water discharged from the scrubber 10 to outboard is a first flow rate. Furthermore, the calculating unit 20 may calculate in advance a value of a second dilution ratio α2 calculated based on the pH1, the pH2, and the pH3, if a flow rate of washing water discharged from the scrubber 10 to outboard is a second flow rate. Also, the recording unit 30 may record the value of the first dilution ratio and the value of the second dilution ratio.

The calculating unit 20 may calculate a pH value of water at the predetermined position, using values α1 to αn of the dilution ratio corresponding to a flow rate of washing water discharged from the scrubber 10 to outboard. Note that, 'n' is a natural number. Furthermore, the recording unit 30 may record and associate the washing water flow rate and values α1 to αn of the dilution ratio. Thereby, the recording unit 30 may have a table of dilution ratios α1 to αn with respect to the washing water flow rate.

If the load of the main engine 60 increases, the amount of the exhaust gas increases. It is expected that, if the flow rate of the washing water supplied to the scrubber 10 is constant, the pH value measured by the first pH measuring instrument 12 decreases, and the pH value of water at the predetermined position outboard also lowers. Then, it is sometimes required to increase the flow rate of the washing water supplied to the scrubber 10, in order to make the pH value of the sea water of the position 4 meters from the discharge point 86 of the outlet opening 82 to be larger than or equal to 6.5.

The controlling unit 40 of the present example is connected to the calculating unit 20 via the recording unit 30. Note that, the controlling unit 40 may also be directly connected to the calculating unit 20. The controlling unit 40 controls flow rate of washing water supplied to the scrubber 10, depending on a pH value of water at the predetermined position calculated by the calculating unit 20. For instance, if it is expected that, if the washing water flow rate is maintained constant as it is, the pH value of the sea water of the position 4 meters from the discharge point 86 falls below 6.5, the controlling unit 40 controls the intake pump 74, and increases a flow rate of washing water supplied to the scrubber 10. Note that, if the washing water flow rate increases, the dilution ratio α rises.

The calculating unit 20 may calculate the smallest washing water flow rate required for the pH value of the sea water of the position 4 meters from the discharge point 86 becomes larger than or equal to 6.5, using the pH value of the first pH measuring instrument 12, the pH value of the second pH measuring instrument 14, and the table of the dilution ratios α1 to αn with respect to the washing water flow rate which are measured at any time. Because if the washing water flow rate is increased, the load of the intake pump 74 increases, the amount of increase in the washing water flow rate is preferably the smallest.

In order that the pH value of the sea water of the position 4 meters from the discharge point 86 becomes larger than or equal to 6.5, from [Expression 3] and [Expression 5], it is only necessary to satisfy the following [Expression 6].

$$6.5 \leq pH = -\log_{10}[C2 + (C1-C2)/\alpha] \quad \text{[Expression 6]}$$

From [Expression 4] and [Expression 6], it is only necessary that the dilution ratio α satisfies the following [Expression 7]. It is only necessary that the calculating unit 20 finds the smallest α which satisfies [Expression 7] (that is, the smallest washing water flow rate) from the table of the dilution ratios α1 to αn with respect to the washing water flow rate.

$$(10^{-pH1} - 10^{-pH2})/(10^{-6.5} - 10^{-pH2}) \leq \alpha \quad \text{[Expression 7]}$$

The controlling unit 40 may control the intake pump 74 so as to supply washing water from the intake pump 74 to the scrubber 10, at the smallest washing water flow rate calculated by the calculating unit 20. Also, the controlling unit 40 may control the scrubber 10 so that the scrubber 10 operates at the washing water flow rate. In this way, if the dilution ratio α is measured in advance every changed washing water flow rate, even if the washing water flow rate changes, the pH at the position 4 meters from a discharge point 86 can be known without measuring the dilution ratio α again.

If flow rate of washing water supplied to the scrubber 10 is larger than or equal to a predetermined allowable amount, the controlling unit 40 may also control flow rate of washing water supplied to the scrubber 10 to smaller than or equal to the allowable amount, by decreasing an output of the main engine 60 as a motor which discharges exhaust gas to the scrubber 10. In the scrubber 10, there is a limit pressure of washing water spray pressure in the scrubber 10, and an upper limit of washing water discharging capacity of the scrubber 10. If the washing water flow rate larger than or equal to the allowable amount of the scrubber 10, which exceeds the limit pressure and the upper limit of washing water discharging capacity of the scrubber 10, flows, there is a danger that the scrubber 10 is broken.

Therefore, the controlling unit 40 may control the main engine 60 and decrease the output of the main engine 60. Thereby, the amount of the exhaust gas from the main engine 60 to the scrubber 10 decreases. In other words, by making the washing water flow rate to be smaller than or equal to the allowable amount, while complying that the pH value of the sea water of the position 4 meters from the discharge point 86 is larger than or equal to 6.5, a breakage of the scrubber 10 can be avoided. Note that, the allowable amount of the washing water flow rate of the scrubber 10 is determined in advance at a time of designing the scrubber 10.

The exhaust gas amount emitted from the main engine 60 is an amount that is in accordance with the load of the main engine 60. The main engine 60 is sometimes operated not only for generating a power of the ship 100, but also for generating the electric power necessary for the ship 100. During navigation of the ship 100, it is inconvenient on using the ship 100 to be forced to decrease the load of the main engine 60, due to the washing water flow rate being limited to the allowable amount the washing water flow rate of the scrubber 10. Therefore, provided that the ship 100 is determined to be at anchor, the controlling unit 40 may decrease an output of the main engine 60 as a motor which discharges exhaust gas to the scrubber 10. Also, this matches that the pH value of the position 4 meters from the discharge point 86 is smaller than or equal to 6.5 is a condition required to the ship 100 at anchor.

Figure 3:
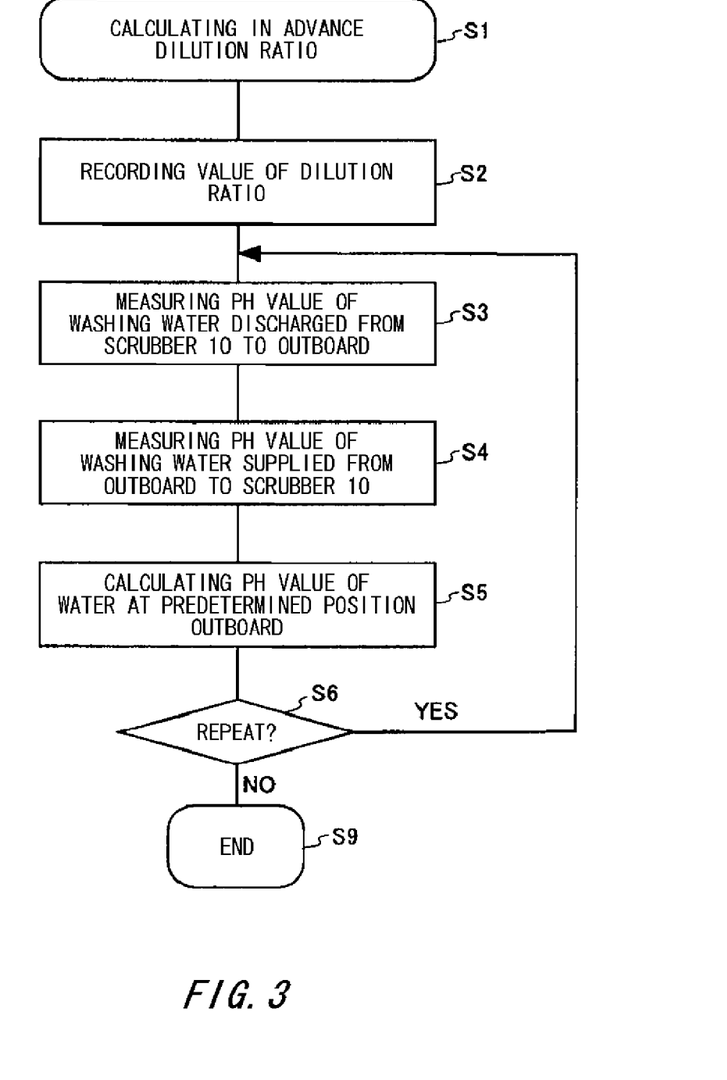
FIG. 3 is a flow diagram of a first embodiment in which a pH value at a position 4 meters from a discharge point 86 is measured using a value of a single dilution ratio α.

FIG. 3 is a flow diagram of a first embodiment in which a pH value at a position 4 meters from a discharge point 86 is measured using a value of a single dilution ratio α. Note that, the flow may be performed at a time of commissioning of the ship 100 having the scrubber 10.

(Step S1)

Step S1 is a step of calculating in advance a value of a dilution ratio, based on the first pH value measured in a step of measuring the pH value of the washing water discharged from the scrubber 10 to outboard using the first pH measuring instrument 12, the second pH value obtained by measuring the pH value of the washing water supplied from outboard to the scrubber 10 using the second pH measuring instrument 14, in a step of measuring the pH value of the washing water discharged from the scrubber 10 to outboard using the first pH measuring instrument 12, and the third pH value of the water at the predetermined position outboard. Specifically, in Step S1, the calculating unit 20 calculates in advance the dilution ratio α using the first to third pH values and the above-described [Expression 1] to [Expression 4].

(Step S2)

Step S2 is a step of recording a value of the dilution ratio α which is calculated in advance. Specifically, the recording unit 30 records the dilution ratio α calculated in advance by the calculating unit 20.

(Step S3)

Step S3 is a step of measuring a pH value of washing water discharged from the scrubber 10 to outboard, after measuring the first pH value. Specifically, the first pH measuring instrument 12 measures a pH value of washing water discharged from the scrubber 10 to outboard. Furthermore, the first pH measuring instrument 12 may input the measured pH value to the calculating unit 20.

(Step S4)

Step S4 is a step of measuring a pH value of washing water supplied from outboard to the scrubber 10, after measuring the second pH value. Specifically, the second pH measuring instrument 14 measures a pH value of washing water supplied from outboard to the scrubber 10. Furthermore, the second pH measuring instrument 14 may input the measured pH value to the calculating unit 20.

(Step S5)

Step S5 is a step of calculating a pH value of water at the predetermined position outboard, based on a pH value of washing water discharged from the scrubber 10 to outboard which is measured after measuring the first pH value, a pH value of washing water supplied from outboard to the scrubber 10 which is measured after measuring the second pH value, and a value of the dilution ratio α recorded. Specifically, by substituting values of the dilution ratio α calculated in advance in Step S2, the pH value measured by the first pH measuring instrument 12 in Step S3, and the pH value measured by the second pH measuring instrument 14 in Step S4 into [Expression 4] and [Expression 5], the calculating unit 20 calculates the pH value of the position 4 meters from the discharge point 86. Thereby, if the dilution ratio α is once measured, by sequentially updating the pH values of the first pH measuring instrument 12 and the second pH measuring instrument 14, pH of the position 4 meters from the discharge point can be known.

(Step S6)

Step S6 is a step of determining whether to repeat Step S3 to Step S5 again or not. Specifically, the controlling unit 40 may determine whether to repeat Step S3 to Step S5 again or not. If YES in Step S6, Step S3 to S5 may be repeated a plurality of times. If NO in Step S6, the flow ends (Step S9).

Figure 4:
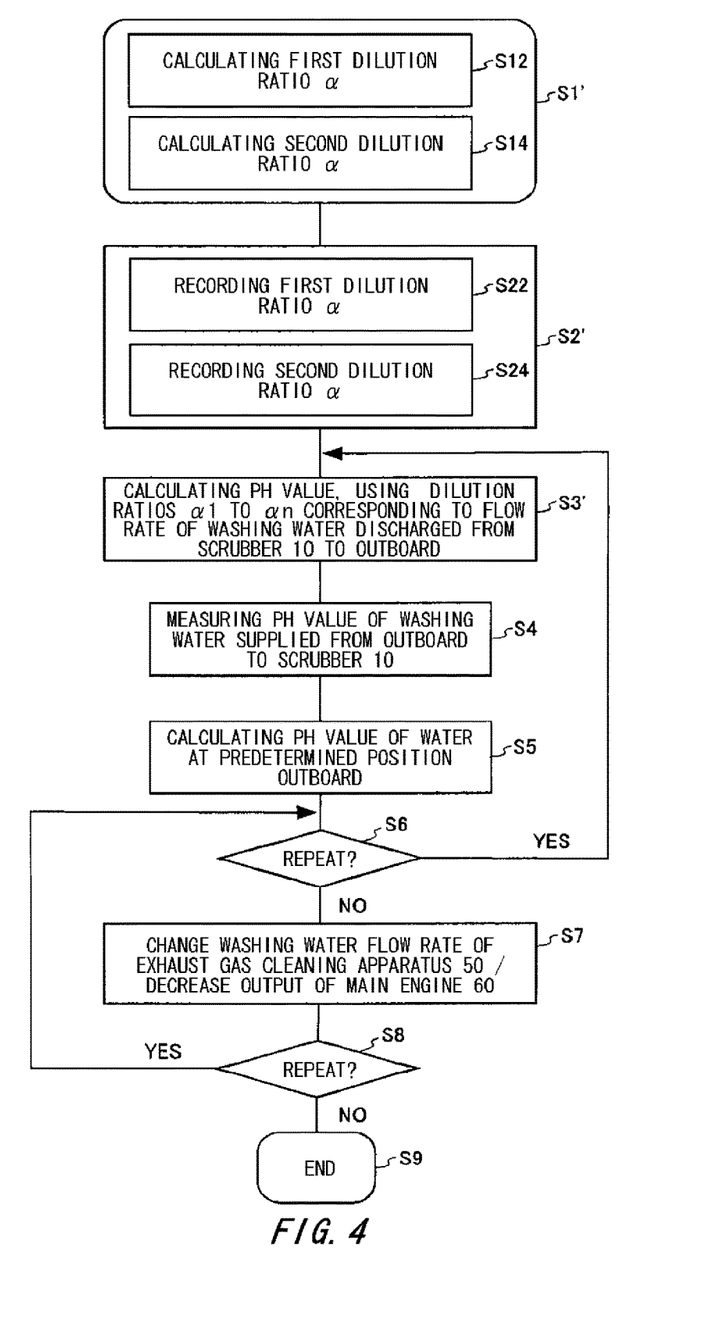
FIG. 4 is a flow diagram of a second embodiment in which a pH value at a position 4 meters from a discharge point 86 is measured using values of a plurality of dilution ratios α1 to αn.

FIG. 4 is a flow diagram of a second embodiment in which a pH value at a position 4 meters from a discharge point 86 is measured using values of a plurality of dilution ratios α1 to αn. Note that, Step S1', Step S2', and Step S3' of the present example are different from Step S1, Step S2, and Step S3 of the first embodiment. Also, the present example may arbitrarily have an additional Step S7. The present example differs from the first embodiment in this point. The points other than that are common to the first embodiment.

(Step S1')

Step S1' of the present example is a step of calculating in advance a value of the dilution ratio α. In Step S1', the calculating unit 20 calculates a value of a first dilution ratio calculated based on the first pH value, the second pH value, and the third pH value, if a flow rate of washing water discharged from the scrubber 10 to outboard is a first flow rate, and a value of a second dilution ratio calculated based on the first pH value, the second pH value, and the third pH value, if a flow rate of washing water discharged from the scrubber 10 to outboard is a second flow rate. Note that, in Step S1' of the present example, the calculating unit 20 may also calculate two or more dilution ratios. That is, the calculating unit 20 may calculate the dilution ratio corresponding to different washing water flow rates. The dilution ratios α1 to αn ('n' is a natural number) may correspond to first to nth flow rates of washing water flow rates.

(Step S2')

Step S2' of the present example is a step in which the recording unit 30 records a plurality of dilution ratios α1 to αn. That is, the recording unit 30 records a table of the dilution ratios α1 to αn with respect to the washing water flow rate.

(Step S3') Step S3' of the present example calculates a pH value of water at the predetermined position outboard, using a value of the dilution ratio corresponding to a flow rate of washing water discharged from the scrubber 10 to outboard. Specifically, the calculating unit 20 calculates the pH value of water at the position 4 meters from a discharge point 86, using the value of the dilution ratio corresponding to a washing water flow rate, among the dilution ratios α1 to αn. In this way, if the dilution ratios a are measured in advance for every changed washing water flow rate, even if the washing water flow rate changes, the pH at the point 4 meters from a discharge point 86 can be known without measuring the dilution ratio α again.

(Step S7)

Step S7 is a step which may be arbitrarily performed. If NO in Step S6, the step advances to Step S7. If YES in Step S6, the step shifts to Step S3'.

Step S7 has a step of controlling flow rate of washing water supplied to the scrubber 10, depending on a pH value calculated in a step of calculating a pH value of water at the predetermined position outboard. Specifically, if it is expected that, if the washing water flow rate is maintained constant as it is, the pH value of the sea water of the position 4 meters from the discharge point 86 falls below 6.5, the controlling unit 40 controls the intake pump 74, and increases a flow rate of washing water supplied to the scrubber 10.

Also, if flow rate of washing water supplied to the scrubber 10 is larger than or equal to a predetermined allowable amount, Step S7 may have a step of decreasing an output of the main engine 60 as a motor which discharges exhaust gas to the scrubber 10 and controlling flow rate of washing water supplied to the scrubber 10 to smaller than or equal to the allowable amount. Specifically, the controlling unit 40 may control the main engine 60 and decrease the output of the main engine 60. Thereby, by making the washing water flow rate to be smaller than or equal to the allowable amount, while complying that the pH value of the sea water of the position 4 meters from the discharge point 86 is larger than or equal to 6.5, a breakage of the scrubber 10 can be avoided. In addition, provided that the ship 100 is determined to be at anchor, Step S7 may also have a step of decreasing an output of the main engine 60 as a motor which discharges exhaust gas to the scrubber 10.

(Step S8)

Step S8 is a a step of determining whether to repeat Step S3', Step S4, and Step S5 and Step S7, or, only Step S7 again or not. Specifically, the controlling unit 40 may determine which step(s) to be repeated again or not. If YES in Step S8, the step returns to Step S6. Step S3', Step S4, and Step S5 may be repeated a plurality of times. After that, the step returns to Step S6 again. If NO in Step S8, the flow ends (Step S9).

While the embodiments of the present invention have been described, the technical scope of the invention is not limited to the above-described embodiments. It is apparent to persons skilled in the art that various alterations and improvements can be added to the above-described embodiments. It is also apparent from the scope of the claims that the embodiments added with such alterations or improvements can be included in the technical scope of the invention.

The operations, procedures, steps, and stages of each process performed by an apparatus, system, program, and method shown in the claims, embodiments, or diagrams can be performed in any order as long as the order is not indicated by "prior to," "before," or the like and as long as the output from a previous process is not used in a later process. Even if the process flow is described using phrases such as "first" or "next" in the claims, embodiments, or diagrams, it does not necessarily mean that the process must be performed in this order.

EXPLANATION OF REFERENCES

10: scrubber,
12: first pH measuring instrument,
14: second pH measuring instrument,
20: calculating unit,
30: recording unit,
40: controlling unit,
50: exhaust gas cleaning apparatus,
60: main engine,
72: inlet opening,
74: intake pump,
78: chimney,
82: outlet opening,
84: discharge pump,
86: discharge point,
90: small ship,
92: operator,
94: surveying instrument,
96: sampling container,
100: ship

What is claimed is:

1. An apparatus provided inside a ship having a scrubber and an engine which discharges gas to the scrubber, comprising:
 a first pH measuring instrument which measures a pH value of washing water discharged from the scrubber to outboard at the ship's overboard discharge;
 a second pH measuring instrument which measures a pH value of sea water at the ship's inlet; and
 a controlling unit which, controls a flow rate of the sea water or an output of the engine based on the pH value measured by the first pH measuring instrument and the pH value measured by the second pH measuring instrument.

2. The apparatus according to claim 1, further comprising:
 a calculating unit that calculates a pH value of water at a predetermined position outboard, based on the pH value measured by the first pH measuring instrument and the pH value measured by the second pH measuring instrument, wherein
 the controlling unit controls the flow rate of the sea water or the output of the engine based on the pH value calculated by the calculating unit.

3. The apparatus according to claim 2, wherein
 the controlling unit controls a flow rate of the sea water supplied to the scrubber, depending on the pH value of the water at the predetermined position calculated by the calculating unit.

4. The apparatus according to claim 2, wherein
 the calculating unit calculates the pH value of the water at the predetermined position outboard, based on a dilution ratio which indicates a ratio by which the washing water discharged to outboard is diluted at the predetermined position outboard, the pH value measured by the first pH measuring instrument, and the pH value measured by the second pH measuring instrument.

5. A method used inside a ship having a scrubber and an engine which discharges gas to the scrubber, comprising:
 measuring a first pH value of washing water discharged from the scrubber at the ship's overboard discharge;
 measuring a second pH value of sea water at the ship's inlet; and
 controlling a flow rate of the sea water or an output of the engine based on the first pH value and the second pH value.

6. The method according to claim 5, further comprising:
 calculating a pH value of water at a predetermined position outboard, based on the first pH value and the second pH value, wherein
 the controlling is further based on the calculated pH value of the water at the predetermined position.

7. The method according to claim 6, wherein
 the controlling includes controlling a flow rate of the sea water supplied to the scrubber based on the first pH value, the second pH value, and the calculated pH value of the water at the predetermined position.

8. The method according to claim 6, wherein
 the calculating is further based on a dilution ratio which indicates a ratio by which the washing water discharged to outboard is diluted at the predetermined position outboard.

* * * * *